United States Patent [19]
Hassanein

[11] Patent Number: 6,100,082
[45] Date of Patent: Aug. 8, 2000

[54] PERFUSION APPARATUS AND METHOD INCLUDING CHEMICAL COMPOSITIONS FOR MAINTAINING AN ORGAN

[76] Inventor: Waleed H. Hassanein, 36 Dartmouth, Apt. 1209, Malden, Mass. 02148

[21] Appl. No.: 08/936,062

[22] Filed: Sep. 23, 1997

[51] Int. Cl.[7] .................................................. C12M 3/00
[52] U.S. Cl. .................................... 435/284.1; 435/286.5; 435/304.1; 607/3
[58] Field of Search .......................... 422/46; 435/284.1, 435/286.5, 304.1; 607/3

[56] References Cited

U.S. PATENT DOCUMENTS

| | | |
|---|---|---|
| 3,738,914 | 6/1973 | Thorne et al. . |
| 3,995,444 | 12/1976 | Clark et al. ........................... 435/284.1 |
| 5,362,622 | 11/1994 | O'Dell et al. ............................... 435/1 |
| 5,472,876 | 12/1995 | Fahy ...................................... 435/284.1 |
| 5,494,822 | 2/1996 | Sadri ..................................... 435/284.1 |
| 5,498,427 | 3/1996 | Menasche ................................ 424/678 |
| 5,586,438 | 12/1996 | Fahy ........................................... 62/78 |
| 5,599,173 | 2/1997 | Chen et al. . |
| 5,716,378 | 2/1998 | Minten ......................................... 607/3 |
| 5,770,149 | 6/1998 | Raible ......................................... 422/46 |
| 5,786,136 | 7/1998 | Mayer ......................................... 435/12 |
| 5,807,737 | 9/1998 | Schill et al. .......................... 435/284.1 |

FOREIGN PATENT DOCUMENTS

| | | | |
|---|---|---|---|
| 0 376 763 | 7/1990 | European Pat. Off. ......... | A01N 1/02 |
| WO 88 05261 | 7/1988 | WIPO .............................. | A01N 1/02 |
| WO 95 31897 | 11/1995 | WIPO .............................. | A01N 1/02 |
| WO 96 29865 | 10/1996 | WIPO .............................. | A01N 1/02 |
| WO 97 46091 | 12/1997 | WIPO .............................. | A01N 1/02 |

OTHER PUBLICATIONS

Eiseman e al., "A disposable liver perfusion chamber", Surgery, No. 6, Dec. 1966 pp. 1163–1166.

Barinov, E.F., "Hormonal–metabolic disturbances during biological preservation of the heart", Chemical Abstracts, 99(9) Abstract No. 65043 (Aug. 29, 1983). Fiziol. ZH., 29(3):293–299 (1983).

Hulsmann, W.C., et al. "Loss of cardiac contractility and severe morphologic changes by acutely lowering the pH of the perfusion medium: protection by fatty acids", Chemical Abstracts, 1 12(21) Abstract No. 196098 (May 21, 1990). Biochem. Biophys. Acta., 1033(2):214–218 (1990).

Grynberg, A., et al. "Fatty acid oxidation in the heart", Chemical Abstracts, 125(21) Abstract No. 271077 (Nov. 18, 1996). J. Cardiovasc. Pharmacol., 28 (supp 1):S11–S17 (1996).

Probst, I. et al. "Carbohydrate and fatty acid metabolism of cultured adult cardiac myocytes." Chemical Abstracts, 104(25) Abstract No. 222497 (Jun. 23, 1986). Am J. Physiol., 250 (5) Pt. 2:H853–H860 (1986).

Chien, et al., "Canine Lung Transplantation After More Than Twenty–four Hours of Normothermic Preservation," The Journal of Heart and Lung Transplantation, vol. 16, No. 3, Mar. 1997, pp. 340–351.

Chien, et al., "Functional Studies of the Heart During a 24–Hour Preservation Using a New Autoperfusion Preparation," The Journal of Heart and Lung Transplantation, vol. 10, No. 3, May/Jun. 1991, pp. 401–408.

Chien, et al., "A Simple Technique For Multiorgan Preservation," The Journal of Thoracic and Cardiovascular Surgery, vol. 95, No. 1, Jan. 1988, pp. 55–61.

(List continued on next page.)

Primary Examiner—David A. Redding
Attorney, Agent, or Firm—Hamilton, Brook, Smith & Reynolds, P.C.

[57] ABSTRACT

A perfusion apparatus for maintaining a harvested organ during a preservation period is disclosed. The perfusion apparatus includes a preservation chamber for storing the organ during the preservation period. A perfusion circuit is provided having a first line for providing an oxygenated fluid to the organ, and a second line for carrying depleted fluid away from the organ. The perfusion apparatus also includes a device operably associated with the perfusion circuit for maintaining the organ at a substantially normothermic temperature. Moreover, the perfusion apparatus maintains the organ in a viable state.

36 Claims, 3 Drawing Sheets

OTHER PUBLICATIONS

Philippe Menasché, et al., "Improved Recovery of Heart Transplants With A Specific Kit of Preservation Solutions," *The Journal of Thoracic and Cardiovascular Surgery*, vol. 105, No. 2, Feb. 1993, pp. 353–363.

Vinten–Johansen, et al., "Reduction in Surgical Ischemic–Reperfusion Injury With Adenosine and Nitric Oxide Therapy," *Annals of Thoracic Surgery*, No. 60, 1995, pp. 852–857.

Lasley, et al., "Protective Effects of Adenosine in the Reversibly Injured Heart," *Annals of Thoracic Surgery*, No. 60, 1995, pp. 843–846.

Wicomb, et al., "Cardiac Transplantation Following Storage of the Donor Heart by a Portable Hypothermic Perfusion System," *The Annals of Thoracic Surgery*, vol. 37, No. 3, Mar. 1984, pp. 243–248.

Hardesty, et al., "Autoperfusion of the Heart and Lungs For Preservation During Distant Procurement," *The Journal of Thoracic and Cardiovascular Surgery*, vol. 93, No. 1, Jan. 1987, pp. 11–18.

Calhoon, et al., "Twelve–Hour Canine Heart Preservation With a Simple, Portable Hypothermic Organ Perfusion Device," *Annals of Thoracic Surgery*, No. 62, 1996, pp. 91–93.

Rao, et al., "Donor Blood Perfusion Improves Myocardial Recovery After Heart Transplantation," *The Journal of Heart and Lung Transplantation*, vol. 16, No. 6, Jun. 1997, pp. 667–673.

Burt, et al., "Myocardial Function After Preservation For 24 Hours," *The Journal of Thoracic and Cardiovascular Surgery*, vol. 92, No. 2, Aug. 1986, pp. 238–246.

Wicomb, et al., "Orthotopic Transplantation of the Baboon Heart After 20 to 24 Hours' Preservation By Continuous Hypothermic Perfusion With An Oxygenated Hyperosmolar Solution," *The Journal of Thoracic and Cardiovascular Surgery*, vol. 83, No. 1, Jan. 1992, pp. 133–140.

Chambers, et al., "Long–Term Preservation of the Heart: The Effect of Infusion Pressure During Continuous Hypothermic Cardioplegia," *The Journal of Heart and Lung Transplantation*, vol. 11, No. 4, Part 1, Jul./Aug. 1992, pp. 665–675.

Yland, et al., "New Pulsatile Perfusion Method for Non––Heart–Beating Cadaveric Donor Organs: A Preliminary Report," *Transplantation Proceedings*, vol. 25, No. 6, Dec. 1993, pp. 3087–3089.

Segel, et al., "Posttransplantation Function of Hearts Preserved With Fluorochemical Emulsion," *The Journal of Heart and Lung Transplantation*, vol. 13, No. 4, Jul./Aug. 1994, pp. 669–680.

Pearl, et al., "Loss of Endothelium–Dependent Vasodilatation and Nitric Oxide Release After Myocardial Protection With University of Wisconsin Solution," *The Journal of Thoracic and Cardiovascular Surgery*, vol. 107, No. 1, Jan. 1994, pp. 257–264.

Lefer, et al., "Attenuation of Myocardial Ischemia–Reperfusion Injury With Nitric Oxide Replacement Therapy," *Annals of Thoracic Surgery*, No. 60, 1995, pp. 847–851.

Seccombe, et al., "Coronary Artery Endothelial Function After Myocardial Ischemia and Reperfusion," *Annals of Thoracic Surgery*, No. 60, 1995, pp. 778–787.

Hartman, J. Craig, "The Role of Bradykinin and Nitric Oxide in the Cardioprotective Action of ACE Inhibitors," *Annals of Thoracic Surgery*, No. 60, 1995, pp. 789–792.

Rinder, et al., "Blockade of C5a and C5b–9 Generation Inhibits Leukocyte and Platelet Activation During Extracorporeal Circulation," *The Journal of Clinical Investigation, Inc.*, vol. 96, Sep. 1995, pp. 1564–1572.

Aoki, et al., "Anti–CD18 Attenuates Deleterious Effects of Cardiopulmonary Bypass and Hypothermic Circulatory Arrest in Piglets," *J Card Surg*, vol. 10, 1995, pp. 407–417.

Rosenkranz, Eliot R., "Substrate Enhancement of Cardioplegic Solution: Experimental Studies and Clinical Evaluation," *Annals of Thoracic Surgery*, vol. 60, 1995, pp. 797–800.

Engelman, et al., "Influence of Steroids On Complement and Cytokine generation After Cardiopulmonary Bypass," *Annals of Thoracic Surgery*, vol. 60, 1995, pp. 801–804.

Boyle, et al., "Ischemia–Reperfusion Injury," *Annals of Thoracic Surgery*, vol. 64, 1997, pp. 524–530.

Li, et al., "Functional Recovery In Rabbit Heart After Preservation With a Blood Cardioplegic Solution and Perfusion," *The Journal of Heart and Lung Transplantation*, vol. 12, No. 2, Mar./Apr. 1993, pp. 263–270.

Seccombe, et al., "Coronary Artery Endothelial Function After Myocardial Ischemia and Reperfusion," *Annals of Thoracic Surgery*, vol. 60, 1995, pp. 778–788.

Mankad, et al., "Endothelial Dysfunction Caused By University of Wisconsin Preservation Solution In the Rat Heart," *The Journal of Thoracic and Cardiovascular Surgery*, vol. 104, No. 6, Dec. 1992, pp. 1618–1624.

Sunamori, et al., "Relative Advantages of Nondepolarizing Solution to Depolarizing University of Wisconsin Solution in Donor Heart Preservation," *Transplantation Proceedings*, vol. 25, No. 1, Feb. 1993, pp. 1613–1617.

Pinsky, et al., "Restoration of the cAMP Second Messenger Pathway Enhances Cardiac Preservation for Transplantation in a Heterotopic Rat Model," *The American Society for Clinical Investigation, Inc.*, vol. 92, Dec. 1993, pp. 2994–3002.

Richens, et al., "Clinical Study of Crystalloid Cardioplegia vs Aspartate–Enriched Cardioplegia Plus Warm Reperfusion For Donor Heart Preservation," *Transplantation Proceedings*, vol. 25, No. 1, Feb. 1993, pp. 1608–1610.

Finn, et al., "Effects of Inhibition of Complement Activation Using Recombinant Soluble Complement Receptor 1 On Neutrophil CD11B/CD18 and L–Selectin Expression and Release of Interleukin–8 and Elastase In Simulated Cardiopulmonary Bypass," *The Journal of Thoracic and Cardiovascular Surgery*, vol. 111, No. 2, Feb. 1996, pp. 451–459.

Wicomb, et al., "24–Hour Rabbit Heart Storage With UW Solution," *Transplantation Proceedings*, vol. 48, No. 1, Sep. 1989, pp. 6–9.

Menasché, et al., "Experimental Evaluation of Celsior®, A New Heart Preservation Solution," *European Journal of Cardiothoracic Surgery*, vol. 8, 1994, pp. 207–213.

Ferrera, et al., "Comparison of Different Techniques of Hypothermic Pig Heart Preservation," *Annals of Thoracic Surgery*, vol. 57, 1994, pp. 1233–1239.

Gundry, et al., "Successful Transplantation of Hearts Harvested 30 Minutes After Death From Exsanguination," *Annals of Thoracic Surgery*, vol. 53, 1992, pp. 772–775.

Demertzis, et al., "University of Wisconsin Versus St. Thomas' Hospital Solution For Human Donor Heart Preservation," *Annals of Thoracic Surgery*, vol. 55, 1993, pp. 1132–1137.

Segel, et al., "Recovery of Sheep Hearts After Perfusion Preservation or Static Storage With Crystalloid Media," *The Journal of Heart and Lung Transplantation*, vol. 17, No. 2, Feb. 1998, pp. 211–221.

The DuPont Merck Pharmaceutical Co., Product Literature For "ViaSpan® (Belzer UW) Cold Storage Solution," Jan. 1996.

Drexler, et al., "Effect of L–Arginine On Coronary Endothelial Function In Cardiac Transplant Recipients," *Circulation*, vol. 89, No. 4, Apr. 1994, pp. 1615–1623.

Sato, et al., "Supplemental L–Arginine During Cardioplegic Arrest and Reperfusion Avoids Regional Postischemic Injury," *The Journal of Thoracic and Cardiovascular Surgery*, vol. 110, No. 2, Aug. 1995, pp. 302–314.

Article "The Effect Of Machine Perfusion Preservation Versus Cold Storage On The Function Of Kidneys From Non–Heart–Beating Donors," *Transplantation Proceedings*, vol. 57, No. 2, Jan. 1994, pp. 293–294.

Tesi, et al., "Pulsatile Kidney Perfusion For Preservation And Evaluation: Use Of High–Risk Kidney Donors To Expand The Donor Pool," *Transplantation Proceedings*, vol. 25, No. 6, Dec. 1993, pp. 3099–3100.

Shirakura, et al., "Multiorgan Procurement From Non–Heart–Beating Donors By Use Of Osaka University Cocktail, Osaka Rinse Solution, and the Portable Cardiopulmonary Bypass Machine," *Transplantation Proceedings*, vol. 25, No. 6, Dec. 1993, pp. 3093–3094.

Matsuno, et al., "Effectiveness of Machine Perfusion Preservation As A Viability Determination Method For Kidneys Procured From Non–Heart–Beating Donors," *Transplantation Proceedings*, vol. 26, No. 4, Aug. 1994, pp. 2421–2422.

Habazettl, et al., "Improvement In Functional Recovery Of The Isolated Guinea Pig Heart After Hyperkalemic Reperfusion With Adenosine," *The Journal of Thoracic and Cardiovascular Surgery*, vol. 111, No. 1, Jan. 1996, pp. 74–84.

Menasché, Philippe, "The Inflammatory Response To Cardiopulmonary Bypass And Its Impact On Postoperative Myocardial Function," *Current Opinion In Cardiology*, vol. 10, 1995, pp. 597–604.

Chien, S., et al., "A Simple Technique For Multiorgan Preservation," J Thorac Cardiovasc Surg, 1988; 95: 55–61.

Calhoon, J., et al., "Twelve–Hour Canine Heart Preservation With a Simple, Portable Hypothermic Organ Perfusion Device," Ann Thorac Surg, 1996; 62: 91–93.

Yland, M.J., et al., "New Pulsatile Perfusion Method for Non–Heart–Beating Cadaveric Donor Organs: A Preliminary Report," Transplantation Proceedings, vol. 25, No. 6 (Dec.) 1993, pp. 3087–3090.

PERFUSION APPARATUS AND METHOD INCLUDING CHEMICAL COMPOSITIONS FOR MAINTAINING AN ORGAN

BACKGROUND OF THE INVENTION

1. Technical Field

The present invention relates to an organ perfusion apparatus, and more particularly, to a perfusion apparatus and method including chemical compositions for extending the preservation period of a donor organ which has been harvested for transplantation.

2. Discussion

It is estimated that one of every four patients listed for cardiac transplantation dies awaiting the availability of a suitable organ donor. While progress has been made for making more donor organs available, the development of successful techniques for donor heart preservation has not kept pace with the demand for cardiac transplantation. With improvements in patient survival and the development of new immunosuppressive agents, heart transplantation has become more feasible, making the problem of organ supply even more critical. Despite the acceptable clinical results obtained with the current donor organ and donor heart preservation techniques, one of the major challenges that remains is the current inability to safely preserve the donor heart for more than four hours. Extending the preservation period beyond four hours using current preservation techniques significantly increases the risk of failure during or after transplantation. This four hour limitation also restricts the geographic area from which donor hearts can be transported for successful transplantation.

Current donor organ preservation protocols utilize hypothermic arrest and storage in a chemical perfusate for maintaining the heart (non-beating) for up to four hours. However, these protocols utilize a variety of crystalloid-based cardioplegic solutions that do not completely protect the donor heart from myocardial damage resulting from ischemia and other reperfusion injuries. In addition to myocardial damage, ischemia and reperfusion may also cause coronary vascular endothelial and smooth muscle injury leading to coronary vasomotor dysfunction. (Ischemia is generally defined as an insufficient blood supply to the heart muscle.)

These current preservation techniques involve arresting the heart with a crystalloid-based cardioplegic solution and storing the heart on ice in the same solution until implantation. Techniques have also been developed for perfusing the heart with the storage solution in the hypothermic state. The heart can then be transported in this hypothermic state for up to four hours until implantation. The most common cardioplegic preservation solutions used are The University of Wisconsin Solution (UW), St. Thomas Solution, and the Stanford University Solution (SU). However, all of the protocols utilizing these solutions require hypothermic arrest, and do not overcome the problems of myocardial damage.

As is well known in the art, for optimal donor heart preservation, the following principles apply: a) Minimization of cell swelling and edema; b) prevention of intracellular acidosis; c) prevention of injury caused by oxygen free radicals; and d) provision of substrate for regeneration of high-energy phosphate compounds and ATP during reperfusion. The current method of hypothermic arrest and storage preservation has been shown to result in cell swelling, intra- and extracellular acidosis, and a degradation of high-energy phosphates. Moreover, studies in humans have clearly demonstrated significant endothelial dysfunction following donor heart preservation when utilizing hypothermic arrest and storage protocols. In some instances, an organ which has undergone hypothermic arrest is transplanted into the recipient and cannot be restarted after transplantation. Many times, this is a result of acute graft failure at one or more locations on the heart. The problem of acute graft failure then requires constant support of the recipient's circulatory system by ventricular assist devices and/or cardiopulmonary bypass until a new donor heart can be located. In some instances, a suitable organ cannot be located in time which results in the death of the recipient. There is also increasing evidence from a number of recent clinical studies that the preservation of metabolic, contractile and vasomotor function is not optimal with current preservation protocols.

Based upon experimental studies, donor blood perfusate has been shown to be a more suitable alternative for clinical donor heart preservation because it provides better substrate, oxygen delivery, endogenous-free radical scavengers, potent buffers, and improved oncotic pressure. Accordingly, it is desirable to achieve prolonged ex-vivo preservation of the donor heart that has been harvested by providing continuous sanguineous perfusion, while maintaining the donor heart in the normal beating state. Such a technique would eliminate the need to arrest the heart for storage in a hypothermic environment, and overcome many of the problems associated with hypothermic arrest and storage.

Therefore, it is further desirable to provide an apparatus and method for creating an extracorporeal circuit for sanguineously perfusing the harvested organ at normothermia for preserving the harvested organ for up to twenty-four hours or longer. Such an apparatus and method would optimally maintain the harvested organ in the beating state during the preservation period to insure pulsatile coronary flow and homogeneous distribution of the substrate. Such an apparatus would also provide the ability to extend the preservation period of the harvested organ beyond the current four hour limit, while avoiding prolonged ischemia, preserving coronary endothelial vasomotor function, and preventing the metabolic degradation of high-energy phosphates.

Additionally, such an apparatus and method would allow for expanding the organ donor pool, increasing the histocompatibility matching time, and potentially reducing the incidents of cardiac allograft vasculopathy. Prolonging the preservation period of the donor heart would have a dramatic impact on the practice of heart transplantation. A worldwide retrieval of organs would be made possible, thus increasing the pool of available organs. Organs would not go unused because of lack of suitable nearby recipients. Moreover, additional time would become available to determine the immunologic and functional characteristics of each organ, thereby reducing the risk of graft failure.

SUMMARY OF THE INVENTION

A goal of the present invention is to provide an apparatus and method for providing optimal and prolonged ex-vivo preservation of the donor organ or heart by implementing a method of continuous sanguinous perfusion in the normal beating state. According to the apparatus and method associated with the present invention, this preservation period can be extended for twenty-four hours or more with the heart maintained in the viable state.

Accordingly, a perfusion apparatus for maintaining a harvested organ during a preservation period is disclosed. The perfusion apparatus includes a preservation chamber for storing the organ during the preservation period. A perfusion circuit is provided having a first line for providing an oxygenated fluid to the organ, and a second line for carrying depleted fluid away from the organ. The perfusion apparatus also includes a device operably associated with the perfusion circuit for maintaining the organ at a substantially normothermic temperature. Moreover, the perfusion apparatus maintains the organ in a viable state.

A method of perfusing an organ or donor heart is also disclosed. The method comprises providing a preservation chamber for containing the organ, and a perfusion circuit operably associated with the preservation chamber. The perfusion circuit includes a first line for delivering fluid to the organ and a second line for carrying fluid away from the organ. The method also includes providing several chemical solutions to the fluid in the perfusion circuit and perfusing the organ or donor heart with the fluid.

Therefore, an object of the present invention is to maintain the donor heart in the beating state during the preservation period to insure homogeneous distribution of the substrate. Maintaining the heart in the beating state also serves to sustain normal metabolic, contractile and endothelial vasomotor function beyond the four hour hypothermic arrest and storage period currently employed for donor heart preservation.

BRIEF DESCRIPTION OF THE DRAWINGS

The various advantages of the present invention will become apparent to one skilled in the art by reading the following specification and appended claims, and by referencing the following drawings in which:

DETAILED DESCRIPTION OF THE INVENTION

Figure 1:
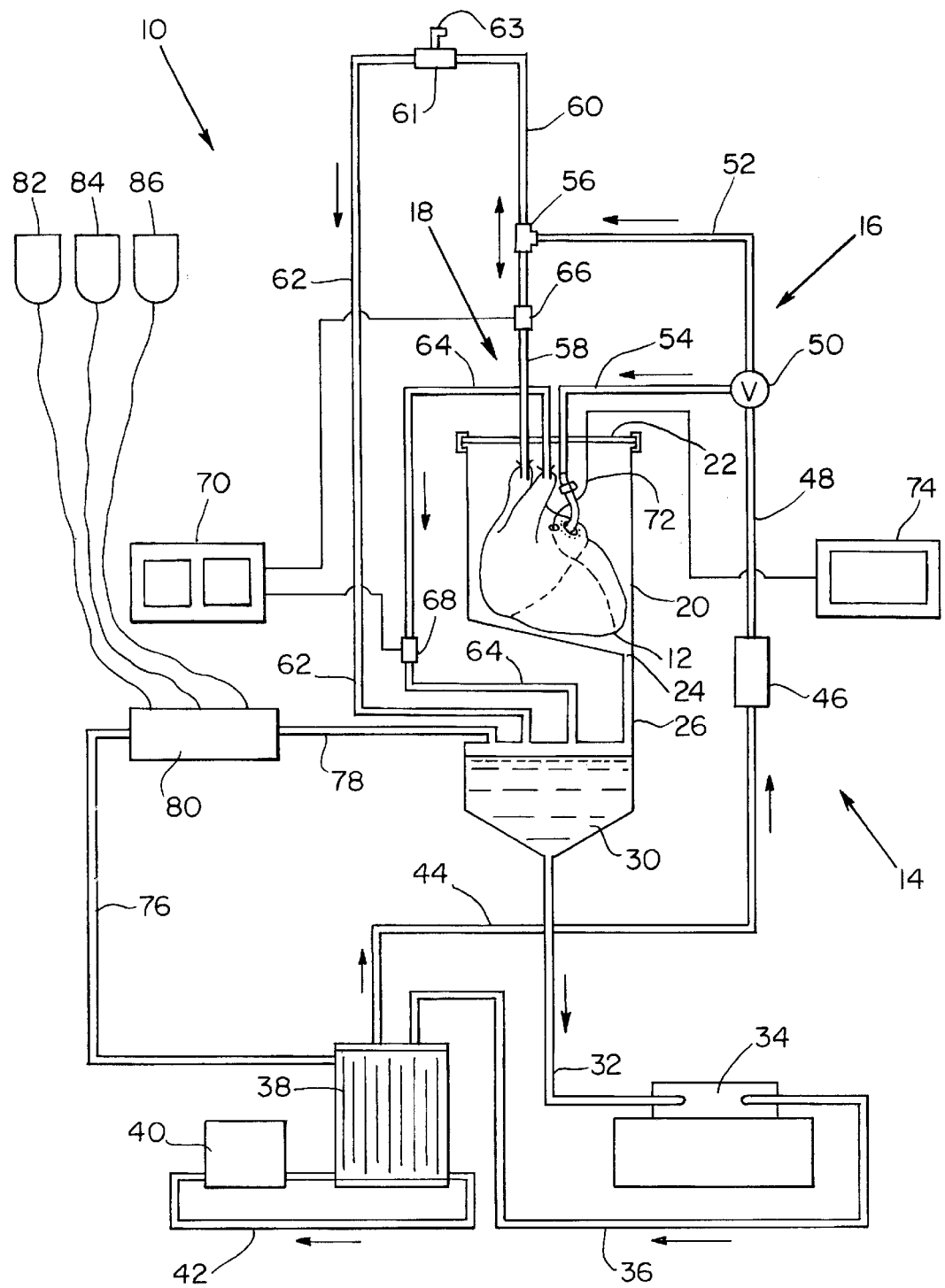
FIG. 1 is a schematic of the perfusion circuit and the components forming the perfusion system according to a preferred embodiment of the present invention.

The present invention is directed to a perfusion apparatus and method for extending the preservation time of a donor organ, such as a human heart, which has been harvested for transplantation. Referring now to FIG. 1, the perfusion system 10 is shown in accordance with the present invention. While FIG. 1 illustrates a schematic of perfusion system 10, it will be appreciated that various modifications to this schematic are within the scope of the present invention. The present invention allows the donor heart to be harvested in the beating state and connected to perfusion system 10 where the organ is maintained in the beating state and provided with a pulsatile, physiologic coronary flow. Accordingly, the donor heart does not have to be arrested prior to its connection with perfusion system 10, thereby eliminating time dependent ischemic injury. Another advantage of the present invention is that the perfusate used to extend the preservation period is comprised primarily of autologous blood which is circulated through the perfusion system 10. Thus, the donor heart is provided with oxygen and essential nutrients during the preservation period which maintains the organ in a viable state. Moreover, cellular waste is carried away from the organ and filtered out of perfusion system 10.

Perfusion system 10 is designed to simulate the human cardiovascular system for maintaining the donor heart 12 in the beating state for periods up to or exceeding 24 hours. As with the human cardiovascular system, perfusion system 10 comprises a closed perfusion circuit 14 for circulating a fluid, comprised of autologous blood and other chemical compositions, to donor heart 12. Accordingly, perfusion circuit 14 includes one or more arterial lines 16 for providing oxygenated perfusion fluid to donor heart 12, and one or more venous lines 18 for carrying depleted perfusion fluid away from donor heart 12. As part of the method of the present invention, the arterial lines 16 are used for perfusing donor organ 12 in the both the non-working and working states. This method of antegrade perfusion will be discussed in more detail below.

With continued reference to FIG. 1, donor heart 12 is shown as being connected to perfusion circuit 14. The donor heart 12 is enclosed within a preservation chamber 20 which is preferably made of a hard, clear plastic to allow for visualization of the preserved organ. While it is preferred that preservation chamber 20 is formed from a plastic material such as LEXAN® plastic, the preservation chamber 20 may also be made of a thick, yet soft flexible plastic in the form of a zipper bag (not shown) to accommodate the contour and shape of donor heart 12. When preservation chamber 20 is a hard plastic container, a plastic cover assembly 22 is used to seal the preservation chamber 20 and to maintain the sterility and humidity of donor organ 12. When a soft plastic preservation chamber (not shown) is employed, a zipper is used to seal the preservation chamber 20 and to protect the organ. A suitable drain 24 is provided at the lowest portion of preservation chamber 20. The drain 24 is connected to a reservoir 30 via drain line 26 to allow for the return of any blood escaping from the organ 12 during the instrumentation period, or from any leakage occurring during the preservation and transport period.

As disclosed, reservoir 30 is designed to contain approximately 1500–3000 ml of fluid. Initially, reservoir 30 is primed with 1500–2500 ml of autologous or cross-matched blood which is then pumped throughout perfusion circuit 14. The reservoir output line 32 is connected to the input of a centrifugal pump 34 which circulates the perfusion fluid through the arterial lines 16 of perfusion circuit 14. The preferred pump for this application is the Biomedicus 550, manufactured by Medtronic, which propels the blood via magnetic field driven cones. While a conventional roller pump may also be used, the magnetic propulsion generated by centrifugal pump 34 is preferable to minimize hemolysis of the blood.

The centrifugal pump 34 propels the blood via pump output line 36 into a membrane oxygenator 38. The blood is oxygenated using a preferred mixture of 95% $O_2$ and 5% $CO_2$ at a rate of 1–2 L/min by membrane oxygenator 38. The preferred oxygenator is a hollow fiber membrane oxygenator, such as the Monolyth manufactured by Sorin Biomedical. While not specifically shown in FIG. 1, membrane oxygenator 38 is provided with the oxygen and carbon dioxide mixture through a regulated oxygen bottle 178. The oxygenator 38 also includes a plurality of ports (not shown) which allow pressurized perfusion fluid to be directed to other devices. A water heater 40 provides warmed water through a water circuit 42 which maintains the fluid within perfusion circuit 14 at about 37° C. (normothermia). The warmed perfusion fluid then maintains donor heart 12 at a normothermic temperature. The oxygenator output line 44 carries the oxygenated and rewarmed fluid to a filter 46. Preferably, the fluid is filtered with a 40–100 micron leukocyte filter, such as the Pall leukocyte depleting filter manufactured by Pall Filters.

The output of filter 46 is connected to a selector valve 50 via filter output line 48. Selector valve 50 may be placed in one of several positions for directing fluid flow to either the initial perfusion line 52 (for antegrade perfusion via the aorta), the left atrium supply line 54 (for antegrade perfusion via the left atrium), or both lines simultaneously (for priming purposes). Additionally, selector valve 50 may be turned off completely. As will be appreciated, lines 48, 54, and at times lines 52 and 58 form the arterial side 16 of perfusion circuit 14. The opposite end of the initial perfusion line 52 is connected into a tee 56 which then branches to aorta line 58 and the afterload column, line 60. A straight connector 61 is used for connecting line 60 with the aorta return line 62. A Luer port 63 is secured to connector 61 which acts as a one-way valve for allowing fluid pumped across connector 61 to flow through aorta return line 62 without siphoning additional fluid from afterload line 60. Luer port 63 operates by allowing air into aorta return line 62 for breaking the siphoning effect of the fluid. Accordingly, the peak of afterload column 60 is formed by connector 61 and Luer port 63.

The distal end of the afterload line 62 is attached to reservoir 30 to allow blood pumped through the aorta 130 to flow back to the reservoir 30. As will be discussed in more detail below, aorta line 58 provides bidirectional flow to and from donor heart 12, depending upon which mode the perfusion system 10 is operating. The height of afterload column 60 is adjustable between a range of vertical positions for selectively changing the afterload pressure against which the heart 12 will beat or pump. Once the fluid pumped through afterload column 60 crosses connector 61, it is returned to reservoir 30 via aorta return line 62. Additionally, a right ventricle return line 64 is connected to the pulmonary artery 132 to return coronary effluent to the reservoir 30. As will be appreciated, lines 58, 60, 62 and 64 form the venous side 18 of perfusion circuit 14.

The aortic flow is measured by an in-line ultrasonic flow probe 66 which is part of aorta line 58. Likewise, an in-line ultrasonic flow probe 68 measures the coronary blood flow through right ventricle return line 64 of coronary effluent from the right ventricle to the reservoir 30. The aortic and coronary flow signals produced by ultrasonic flow probes 66 and 68 are recorded on a two-channel flow meter 70 which assists in monitoring the condition of the preserved organ 12, and the performance of perfusion system 10. The preferred flow meter 70 for use with the present invention is the two-channel flow meter manufactured by Transonic Systems.

The coronary flow is maintained within acceptable physiologic ranges (300–500 ml/min) by adjusting the height of the afterload column 60 above the heart 12. The afterload pressure is maintained at approximately 70 mm of mercury, but may be adjusted as necessary. A micro-tip pressure catheter 72 is inserted into the left ventricle via the left atrium 134 for measuring the intracavitary pressures of donor heart 12. A preferred pressure catheter 72 is of the type manufactured by Millar Instruments. All pressure measurements generated by pressure catheter 72 are recorded and displayed using a digital pressure recording system 74 which also assists in monitoring the condition of the preserved organ 12. As disclosed, pressure recording system 74 is capable of recording and displaying multiple pressure measurements.

One of the ports from oxygenator 38 is connected to a supply line 76 which provides oxygenated blood to a drip manifold 80. As disclosed, three IV bags 82, 84, 86 are connected to drip manifold 80 which provide various chemical compositions for the preserved organ (discussed in more detail below). Drip manifold 80 is known in the art and provides a mechanism for regulating the drip rate of each chemical solution stored in the IV bags 82, 84, 86. A manifold output line 78 carries the blood, enriched with the various chemical solutions to reservoir 30 for circulation to the donor heart 12.

A variety of materials may be used for creating the various lines and components of perfusion system 10. As almost all of the lines and components of perfusion circuit 14 are in constant contact with the blood perfusate, it is desirable to suppress the acute inflammatory response caused by exposure of the blood to extracorporeal artificial surfaces. To alleviate this problem, all of the contact surfaces within perfusion circuit 14 may be coated or bonded with heparin to reduce complement and granulocyte activation. As an alternative, heparin may be directly introduced into the fluid circulating through perfusion circuit 14.

With continued reference to FIG. 1, the operation of perfusion system 10 will be described in more significant detail. As described above, the donor heart is harvested in the beating state and placed into preservation chamber 20. At this point, centrifugal pump 34 is propelling oxygenated and rewarmed blood through line 48. During priming, selector valve 50 is placed into the position which allows blood to flow simultaneously through the initial perfusion line 52 and the left atrium supply line 54. Once the arterial lines 16 of perfusion circuit 14 are sufficiently primed to remove the presence of any air bubbles or air pockets, valve 50 is rotated into the position for supplying initial perfusion line 52 with fluid. Aortic line 58 can then be connected and secured to the aorta 130 using aortic cannula 120. This procedure allows blood to flow to the aortic line 58 for immediate perfusion of donor heart 12 via the aorta 130 in the non-working beating state. Optionally, afterload line 60 may be clamped for maximizing blood flow into the aorta 130. This procedure of antegrade perfusion via the aorta 130 is performed for approximately 10–15 minutes to allow for donor organ stabilization and to provide a period for instrumentation. During this instrumentation period, the remaining flow lines are connected to donor heart 12. More specifically, the connection between aorta line 58 and the aorta 130 is completed, supply line 54 is connected to the left atrium 134, and the right ventricle return line 64 is connected to the pulmonary artery 132. The pulmonary veins, superior, and inferior vena cavae are then tied closed using #0 silk suture. During the initial connection protocol, any blood overflow is contained within preservation chamber 20 and returned to reservoir 30 via drain line 26.

At the end of the stabilization period, the flow to the aorta 130 is reduced by rotating selector valve 50 to the normal operating position which simultaneously and gradually increases the flow to the left atrium 134 via left atrium supply line 54 and gradually shuts off flow through initial perfusion line 52. Afterload line 60 is also unclamped. This procedure then switches the donor heart 12 from the non-working state into the working state, in which blood is pumped through the venous lines 18 of perfusion circuit 14 by the donor heart 12. It should be specifically noted that donor heart 12 remains beating at all times. Blood flow to donor heart 12 through arterial lines 16 is assisted by centrifugal pump 34. The donor heart 12 is allowed to beat against an afterload pressure created by the vertical position of afterload column 60 above the preservation chamber 20 thereby generating a pulsatile coronary flow. Additionally, oxygenated blood is provided to the coronary vascular system, and deoxygenated blood from the coronary vascular system is pumped from the right ventricle into the pulmonary artery return line 64 and returned to reservoir 30. At this point, donor heart 12 can be maintained in the viable beating state for the duration of the preservation period.

While the perfusion system 10 has been specifically described for preserving a heart, the apparatus and method associated with the present invention is particularly well suited for extending the preservation time for any solid organ by eliminating lines 52, 58, 60 and 62, and using line 54 to cannulate the organ's artery, and line 64 to cannulate the vein of the preserved organ. Accordingly, organs including the kidney, liver, lung, pancreas, and small intestine can be preserved for extended periods of time by perfusion system 10.

Figure 2:
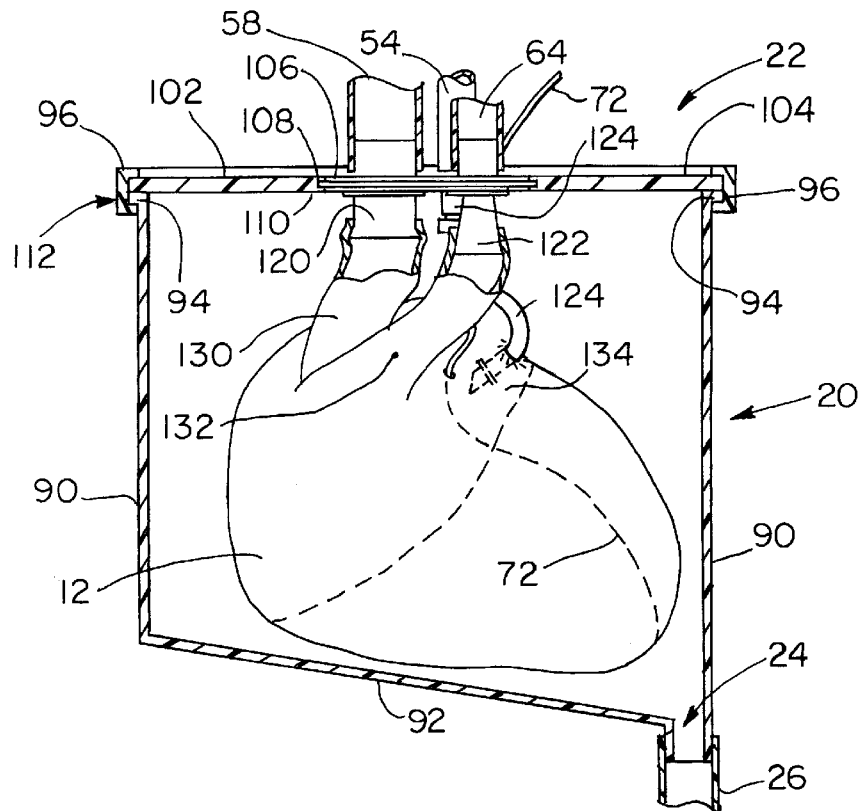
FIG. 2 is a cross-sectional view of the preservation chamber for maintaining the donor heart in the beating state according to a preferred embodiment of the present invention.

Turning now to FIG. 2, the preservation chamber 20 and the connections between the various cannula and the donor heart 12 are shown in more detail. As disclosed, preservation chamber 20 has an open top, and is defined by a generally cylindrical side wall 90 and a sloped bottom 92 which promotes the flow of fluid into drain 24 for return to reservoir 30 via line 26. Sloped bottom 92 further accommodates the donor organ 12 in a more correct anatomical position during the instrumentation and preservation periods. The top of cylindrical side wall 90 includes an outwardly protruding flange 94 around its circumference for providing an additional surface for receiving the cover assembly 22.

Figure 3:
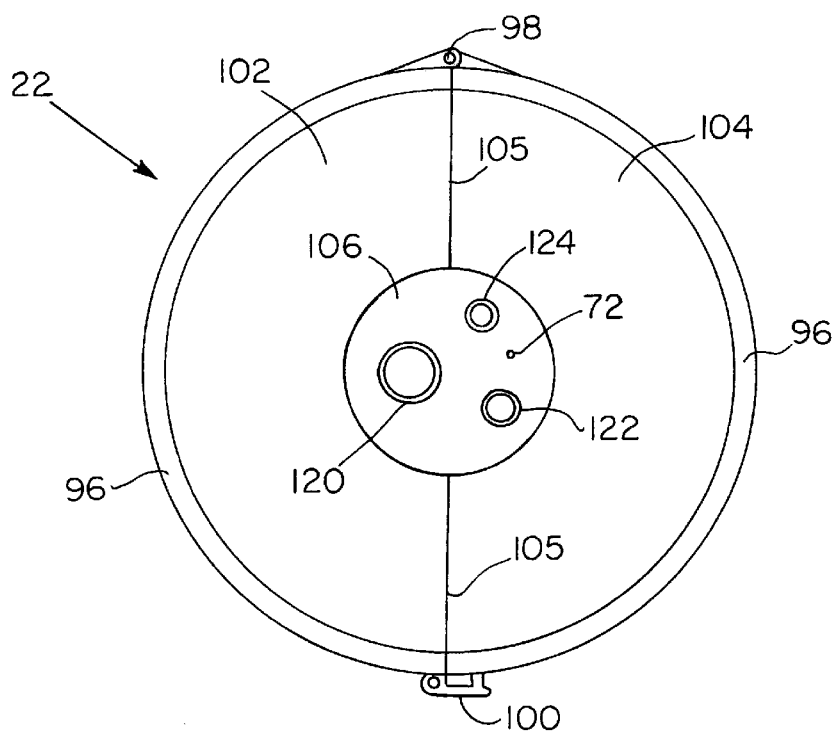
FIG. 3 is a top plan view of the cover assembly utilized with the preservation chamber according to the present invention.

Referring now to FIGS. 2 and 3, the components of cover assembly 22 are described in more detail. The outer circumference of cover assembly 22 is defined by a clamping ring 96 including two halves which are connected by a hinge 98. The two halves of clamping ring 96 can be releasably secured via snap lock 100. The remaining portion of the cover assembly 22 is formed by first cover 102 and second cover 104 which together form a circular cover plate having an aperture in the center thereof for receiving cannula plate 106. Clamping ring 96 has a generally U-shaped cross-section which is designed for receiving flange 94 and first and second covers 102, 104 for creating a tight seal as shown in FIG. 2. The abutting edges 105 between first cover 102 and second cover 104 include a tongue-and-groove structure (not shown) for providing additional rigidity and sealing capability to cover assembly 22. In a similar fashion, cannula plate 106 includes an annular tongue 108 which fits within an annular groove 110 formed within first cover 102 and second cover 104 for securing cannula plate 106 within cover assembly 22. While the tongue-and-groove arrangement associated with abutting edges 105 is not specifically shown, one skilled in the art will readily appreciate that this arrangement is substantially similar to the arrangement of annular tongue 108 and annular groove 110.

While several variations exist for arranging cover assembly 22, it is preferred that first cover 102 and second cover 104 are permanently secured to their respective side of clamping ring 96. In this fashion, an annular channel 112 remains along the lower inside circumference of clamping ring 96 for receiving flange 94 when the cover assembly 22 is placed on top of preservation chamber 20. Upon properly engaging annular channel 112 with flange 94, both halves of clamping ring 96 can be brought together for securely fastening snap lock 100 so that the cover assembly 22 may properly maintain the sterility and humidity of the enclosed organ.

Another advantage provided by cover assembly 22 is that cannula plate 106 is a separate component which interlocks with first and second covers 102, 104 of cover assembly 22 upon installation and securement thereof. As such, the various cannulas secured within cannula plate 106 can be attached to the appropriate locations on the organ 12 prior to installing cover assembly 22. The cannula plate 106 also positions each cannula in the proper location while the organ 12 is connected to perfusion system 10. More specifically, cannula plate 106 includes a first aperture for receiving the aortic cannula 120, a second aperture for receiving the arterial cannula 122, a third aperture for receiving the left atrial cannula 124, and a fourth aperture for receiving the pressure catheter 72. Each individual cannula is snapped into cannula plate 106 to provide a secure connection. It is further contemplated that each cannula has a standard sized top tube for snapping into the cannula plate 106, and a variably sized flared lower tube for fitting within its associated artery or vein. Therefor, if a cannula with a smaller or larger lower tube is required, it can be swapped into cannula plate 106 without removing the other cannulas. Accordingly, the design of cannula plate 106 provides a modular component which easily and securely integrates with cover assembly 22.

In operation, the fully assembled cannula plate 106 is held in proximity to the beating organ 12 so that aorta 130 can be connected to aortic cannula 120, the pulmonary artery 132 can be connected to the arterial cannula 122, and the left atrial cannula 124 can be properly inserted and secured within the left atrium 134. Preferably, a surgical grade cable tie (not shown) is used to secure the aorta 130 around the aortic cannula 120, and the pulmonary artery 132 around the arterial cannula 122. The left atrial cannula 124 is secured within the left atrium 134 using size 2-0 prolene surgical suture. As disclosed, the surgical grade cable ties provide a leak-proof seal, and a larger surface area for securing the arteries around their cannula without risk of tearing the tissue. This in turn assists in properly supporting donor heart 12 within preservation chamber 20. In some instances, as with a smaller donor heart 12, the heart may be suspended by the aorta 130 within preservation chamber 20.

After properly securing the organ to the components of cannula plate 106 within preservation chamber 20, each half of lid assembly 22 can be fitted around the outside circumference of cannula plate 106 so that the cover assembly 22 may be secured on top of the preservation chamber 20. The cover assembly 22 and cannula plate 106 then serve to suspend donor heart 12 within the preservation chamber 20. As best shown in FIG. 2, the pulmonary artery line 64 is secured to the arterial cannula 122, the aorta line 58 is connected to the aortic cannula 120, and the left atrium supply line 54 is connected to the left atrial cannula 124. Once all connections have been properly made (approximately 15 minutes), the organ is allowed to beat for approximately 10–15 minutes in the non-working state as described above for stabilization. After the stabilization and instrumentation period, the donor heart is then allowed to beat in the working state against the afterload created by afterload column 60. The preserved organ may continue to beat in the working state for the duration of the preservation period; up to or exceeding 24 hours.

According to the studies performed using perfusion system 10 to support animal hearts, the apparatus and method of the present invention allow the preserved organ to be maintained in the beating state for up to 24 hours or longer with minimal to no myocardial damage. As part of eleven pilot studies using animal hearts, blood electrolytes of donor hearts maintained in the beating state were measured at one hour, six hour and twelve hour intervals. Analysis of the blood electrolytes indicated that the levels of glucose, sodium (Na), chlorine (Cl), potassium (K), calcium (Ca) and $HCO_3$ remained substantially at baseline levels throughout the preservation period. Accordingly, the apparatus and method of the present invention allow a donor heart to be maintained in the viable beating state for periods beyond the current four hour limitation associated with current hypothermic arrest and storage techniques.

Also associated with the apparatus and method of the present invention are three separate chemical solutions operative in the preservation of the organ 12. As disclosed, the three chemical solutions replenish the preserved organ with energy as it is consumed by the cellular activity, maintain the blood electrolytes at physiologic levels, and stimulate the cardiac conduction system for maintaining the donor heart in the beating state during the preservation period. The three chemical solutions are provided to reservoir 30 through drip manifold 80 as previously discussed, which assists in regulating the proper drip rate for each chemical solution. The first solution is stored within IV bag 82, the second solution is stored within IV bag 84, and the third solution is stored within IV bag 86.

Prior to perfusing the organ 12, the perfusion system 10 is primed with 100–250 ml of the primary solution (stored in IV bag 82), 12.5–25 mg of Mannitol (a complex sugar) or a suitable substitute, and preferably 125–250 mg of methylprednisolone sodium succinate or a suitable substitute. The Mannitol acts as an impermeante to increase the osmotic pressure of the perfusate, which serves to minimize or reduce edema formation in the preserved organ. Mannitol also acts as an oxygen or free radical scavenger to attenuate the perturbations of reperfusion injury and extracorporeal perfusion to the preserved organ. Moreover, the Mannitol is especially useful when the perfusate contact surfaces of perfusion circuit 14 are non-heparin bonded. However, Mannitol can still be used within perfusion circuit 14 even when all of its components have heparin bonded surfaces, so that the benefits provided by Mannitol can be fully utilized. The methylprednisolone sodium succinate is a steroid which acts as a cell membrane stabilizer for avoiding cell lysis during reperfusion and also acts as an immunosuppressive agent.

As disclosed, the first solution, or primary solution is a solution comprising sugar and various electrolytes. The first solution is formulated by combining several chemical components with preferably one liter of dextrose, 5% (with a preferred range of between 2.5% and 5% dextrose) in normal saline (0.9 molar sodium chloride). Alternatively, the dextrose may be delivered in half normal saline (0.45 molar sodium chloride). Dextrose is one of the major components needed by the preserved organ for cellular energy and ATP production. The dextrose, a form of glucose, acts by stimulating the aerobic pathway of Glycolysis and the Krebs' cycle; the primary biochemical processes for energy production in the body. To this dextrose solution is added, 4 milliequivalents of potassium chloride (with a preferred range of between 4 meq and 6 meq). The purpose of the potassium chloride is to maintain normal physiologic levels of intra and extra-cellular potassium, thus abolishing arrhythmias (abnormal heart rhythm). Preferably, 35 units of regular insulin (with a preferred range between 20 units and 40 units) are also added to the primary solution. Insulin acts to drive glucose into the cells to make it readily available for the cytoplasmic and mitochondrial metabolic processes. Insulin also drives extracellular potassium into the cells helping in achieving a physiologic potassium level. Preferably, 1.5 grams of calcium chloride (with a preferred range of between 1.0 grams and 1.5 grams of calcium chloride) are also added. Calcium chloride is the primary cation required for myocardial muscle contraction, and its presence in normal physiologic levels is important for maintaining the donor heart in the beating or working state. The calcium chloride also acts as a positive inotrope for increasing the force of myocardial contractility, again required for normal myocardial function during preservation of the donor heart in the beating state. The primary drip solution stored in IV bag 82 is provided to drip manifold 80 at a preferred drip rate of 15 ml/hr (with a preferred range of between 15 ml/hr and 40 ml/hr). In an alternate embodiment of the primary solution, preferably 5 ml of sodium bicarbonate (with a preferred range of between 5 ml and 10 ml) is added to the solution bag to maintain a normal pH of between 7.4–7.5. Thus, the addition of sodium bicarbonate acts to buffer the solution.

The second solution disclosed is preferably a fatty acid solution. In the preferred embodiment, this is achieved with a 20% intralipid solution (with a preferred range of between 10% and 20%). The preferred concentrations of the intralipid solution are currently available from commercial manufacturers. The intralipid solution is provided to drip manifold 80 at a preferred rate of 2 ml/hr (with a preferred range of between 1 ml/hr and 2 ml/hr). The intralipid solution is preferred for use with the present invention due to its high content of fatty acids, which can be directly metabolized by the cells of the donor heart. The fatty acids are the primary source of energy for the myocardial cell. The second source of energy for the myocardial cell is the glucose provided by the first drip solution.

The third solution disclosed is created by mixing preferably 250 ml of normal saline (with a preferred range of between 250 ml and 500 ml) with preferably 4 mg of epinephrine (with a preferred range of between 4 mg and 8 mg of epinephrine). This solution is used to provide the donor heart with base-line levels of catecholamines necessary for normal heart rate and contractility. Epinephrin is also used to maintain the heart rate within a normal physiologic range. Epinephrin works by stimulating the β1 receptors of the sympathetic nervous system in the preserved heart. Studies made in conjunction with the present invention have demonstrated a marked depletion of plasma catecholamines levels after 2–6 hours of preservation in the perfusion system 10, through multiple measurements of serum catecholamine levels. The third solution is provided to drip manifold 80 at a preferred drip rate of 4 ml/hr (with a preferred range of between 2 ml/hr and 12 ml/hr) for maintaining base-line levels of catecholamines. In an alternate embodiment of the third solution or epinephrine solution, preferably 2 ml of sodium bicarbonate (with a preferred range of between 2 ml and 5 ml) is added to the solution bag to maintain a normal pH of between 7.4–7.5. Thus, the addition of sodium bicarbonate acts to buffer the solution.

Because the preserved organ 12 is maintained in the beating state, it is important that the heart be provided with oxygenated blood at the normothermic temperature. The preserved organ should also be provided with a balanced substrate consisting of the three disclosed chemical solutions. Additionally, since the preservation period is up to 24 hours or longer, the preserved organ 12 should be provided with significant amounts of energy and replenished with various chemical compounds for maintaining the normal beating operation.

Figure 4:
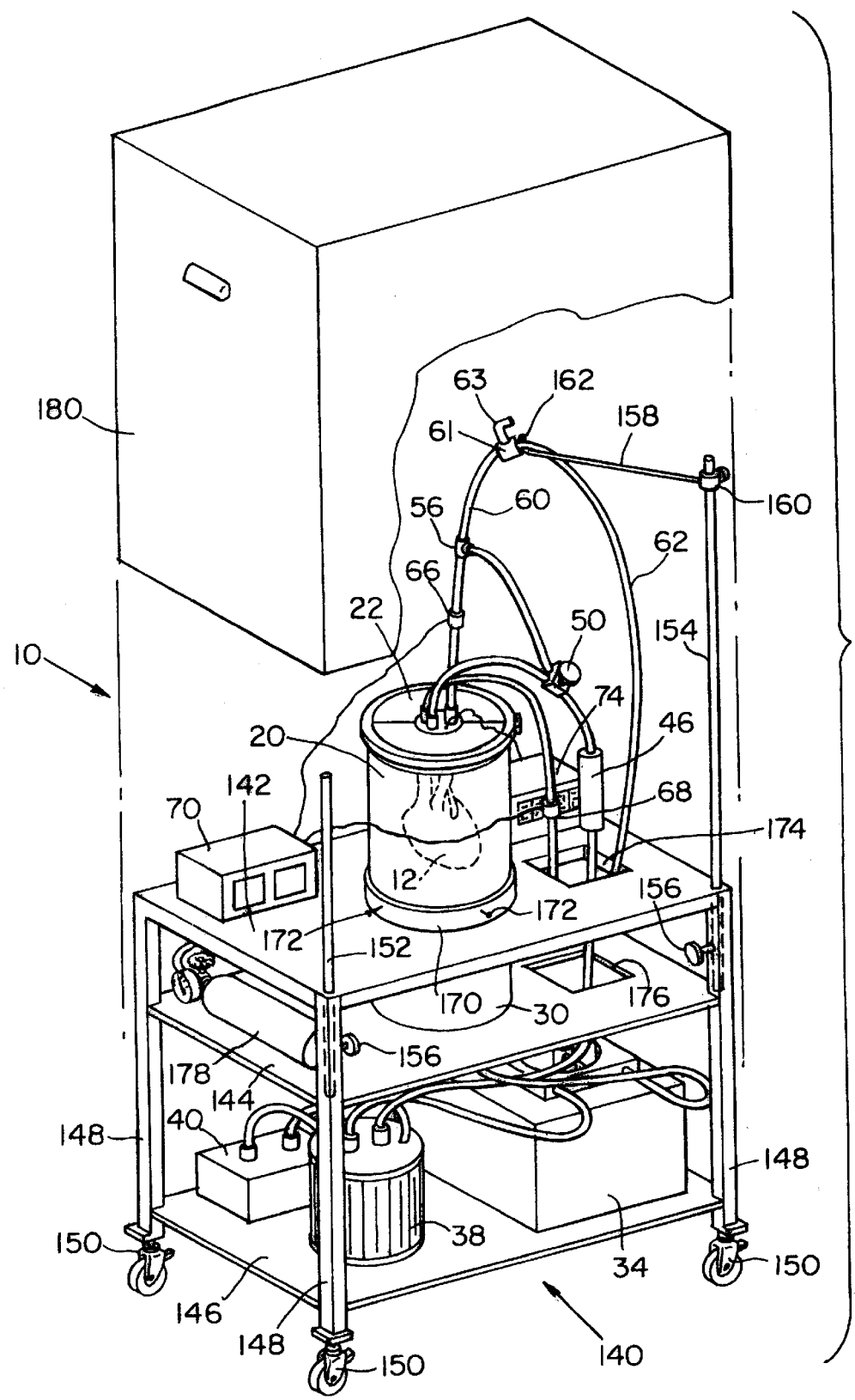
FIG. 4 is a perspective view of the perfusion system installed on a mobile cart for facilitating transportation of the harvested organ, also according to a preferred embodiment of the present invention.

Turning now to FIG. 4, perfusion system 10 is shown as being installed on a mobile cart 140. As disclosed, cart 140 includes a top shelf 142, a middle shelf 144, and a lower shelf 146 which are supported by four posts 148. The lower end of each post 148 includes a locking caster 150. Associated with two of the posts 148 are a pair of adjustable poles 152,154. The height of each pole 152,154 can be adjusted using a threaded locking knob 156. Pole 154 includes an adjustable arm 158 which is primarily intended for supporting lines 60 and 62 for setting the height of the afterload column 60. Adjustable arm 158 also includes a threaded locking knob 160 for setting the height of the adjustable arm 158 and a hook portion 162 at the outboard end thereof for supporting lines 60, 62.

The top shelf 142 of cart 140 includes a circular aperture and annular clamp 170 for receiving and securing preservation chamber 20. As disclosed, preservation chamber 20 is placed into annular clamp 170 and secured with a plurality of thumb screws 172. While not specifically shown, annular clamp 170 and thumb screws 172 may be replaced with a circular clamp operated by a release lever for securing preservation chamber 20. Top shelf 142 is also provided with a square aperture 174 which allows the various lines to pass from the preservation chamber 20 down to the components below. Middle shelf 144 also includes a square aperture 176 which provides a similar function.

As disclosed, reservoir 30 is positioned directly below preservation chamber 20 on the middle shelf 144. Middle shelf 144 also includes an oxygen bottle and regulator 178 for providing the requisite oxygen and carbon dioxide mixture to membrane oxygenator 38. The bottom shelf 146 is particularly well suited for supporting the centrifugal pump 34, membrane oxygenator 38, and water heater 40. Since these are typically the heaviest components associated with perfusion system 10, the location of these components on bottom shelf 146 serves to lower the overall center of gravity which further stabilizes mobile cart 140. Top shelf 142 provides ample surface area for supporting the flow meter 70 and the digital pressure recording system 74. However, additional electronic monitoring and feedback devices could also be supported by top shelf 142 for use with perfusion system 10. Finally, a clear hard plastic cover 180 can be fitted on top of cart 140. Cover 180 allows visual inspection of the components stationed on top shelf 142, while also providing additional protection to the perfusion system 10 and preservation chamber 20.

As will be appreciated by one skilled in the art, mobile cart 140 provides significant enhancement to the overall function of perfusion system 10. More specifically, perfusion system 10 may be wheeled into the operating room from a separate storage location. Additionally, the cart 140 may be easily moved within the operating room or rooms during both organ harvesting and organ implantation. Moreover, the locking casters 150 allow cart 140 to be fixed in one location to prevent unwanted movement. The overall size of mobile cart 140 is such that it can be easily transported in both land based vehicles, such as an ambulance, or within private or commercial aircraft, such as a hospital helicopter or airplane. Accordingly, mobile cart 140 serves to increase the overall efficiency of transporting a harvested organ for implantation into the recipient.

The foregoing discussion discloses and describes exemplary embodiments of the present invention. One skilled in the art will readily recognize from such discussion, and from the accompanying drawings and claims, that various changes, modifications and variations can be made therein without departing from the spirit and scope of the invention as defined in the following claims.

What is claimed is:

1. A perfusion apparatus for maintaining a harvested organ during a preservation period comprising:

a sterile preservation chamber for containing the organ during the preservation period;

a perfusion circuit including at least one line for providing an oxygenated fluid to the organ, and at least one line for carrying depleted fluid away from the organ;

a temperature control means which maintains said organ at a physiologic temperature;

a means for oxygenating said fluid media with a mixture of oxygen and carbon dioxide; and a flow control means for controlling the flow rate of at least part of said fluid media such that the flow rate through said organ is pulsatile and is maintained at a physiologic rate;

wherein said perfusion circuit, said temperature control means, said oxygenation means and said flow control means maintain physiologic levels for temperature, oxygenation and flow rate;

wherein said organ is an integrated element of said perfusion circuit; and wherein said perfusion apparatus is portable.

2. The perfusion apparatus of claim 1 wherein the organ is a heart connected to the perfusion circuit, and wherein said perfusion circuit and said device for maintaining the organ at a normothermic temperature simulate the donor cardiovascular system such that the heart is maintained in the normal beating state by the perfusion apparatus.

3. The perfusion apparatus of claim 2 wherein the perfusion circuit includes an afterload line for maintaining an afterload pressure against which the heart beats.

4. The perfusion apparatus of claim 3 wherein the afterload line may be adjusted for controlling the afterload pressure.

5. The perfusion apparatus of claim 3 wherein the first line is an arterial line splitting into a first supply line connected into the afterload line for supplying the fluid to the aorta, and a second supply line for supplying the fluid to the left atrium, wherein fluid flow into the first and second supply lines is controlled by a multi-position valve.

6. The perfusion apparatus of claim 5 wherein the second line includes an aorta line connected to the afterload line, and a return line connected to the pulmonary artery for carrying fluid away from the organ.

7. The perfusion apparatus of claim 2 further including a pressure sensing device inserted into the heart for measuring an intracavity pressure within the heart.

8. The perfusion apparatus of claim 1 wherein the organ is one of a kidney, liver, lung, pancreas and small intestine.

9. The perfusion apparatus of claim 1 further including a reservoir disposed along the perfusion circuit for storing a predetermined quantity of fluid.

10. The perfusion apparatus of claim 4 wherein the reservoir includes at least one inlet for receiving fluid from the preservation chamber, and one outlet for supplying fluid to the perfusion circuit.

11. The perfusion apparatus of claim 1 wherein the oxygenating means is a membrane oxygenator.

12. The perfusion apparatus of claim 11 wherein a water heater circulates warmed water around the oxygenating means, and wherein heat from the warmed water is exchanged with the circulating fluid for maintaining the circulating fluid and organ at a normothermic temperature.

13. The perfusion apparatus of claim 1 further including a pump for circulating the fluid through the perfusion circuit.

14. The perfusion apparatus of claim 13 wherein the pump is a magnetic induction pump for minimizing hemolysis to the blood.

15. The perfusion apparatus of claim 1 wherein the perfusion circuit includes a filtering device.

16. The perfusion apparatus of claim 1 wherein the perfusion circuit includes at least one flow probe for measuring a flow rate of the fluid from the organ.

17. The perfusion apparatus of claim 1 further including a mobile cart for supporting the preservation chamber and perfusion circuit, and for transporting the organ being preserved by the perfusion apparatus.

18. A portable perfusion apparatus for preserving a harvested donor heart in a viable state comprising:
a preservation chamber for storing the heart during the preservation period;
a perfusion circuit associated with the preservation chamber for circulating a fluid to and from the heart, said perfusion circuit including an arterial line for providing oxygenated fluid to the heart, and at least one venous line for carrying depleted fluid away from the heart;
a reservoir disposed along the perfusion circuit for storing a predetermined quantity of fluid;
a pump for circulating the fluid through the arterial line of the perfusion circuit;
an oxygenating device disposed along the perfusion circuit for oxygenating said fluid media with a mixture of oxygen and carbon dioxide;
a temperature control device operably associated with the perfusion circuit for maintaining the heart at a normothermic temperature;
wherein said perfusion circuit, said pump, said oxygenating device and said temperature control device simulate the donor cardiovascular system by maintaining physiologic levels for temperature, oxygenation and flow rate; and wherein said organ is an integrated element of said perfusion circuit.

19. The perfusion apparatus of claim 18 wherein the reservoir includes at least one inlet for receiving the fluid from the preservation chamber, and an outlet for supplying the fluid to the perfusion circuit.

20. The perfusion apparatus of claim 18 wherein the oxygenating device is a membrane oxygenator.

21. The perfusion apparatus of claim 18 wherein the temperature control device is a water heater for circulating warmed water around the oxygenating device, and wherein heat from the warmed water is exchanged with the circulating fluid for maintaining the circulating fluid and heart at a normothermic temperature.

22. The perfusion apparatus of claim 18 wherein the arterial line includes a first supply line connected into an afterload line for supplying fluid to the aorta during an antegrade perfusion period, and a second supply line for supplying fluid to the left atrium during a perfusion period, wherein fluid flow into the first and second supply lines is controlled by a multi-position valve.

23. The perfusion apparatus of claim 18 wherein the venous line includes an afterload line connected to the aorta for receiving fluid pumped from the left ventricle, and a return line connected to the pulmonary artery for receiving fluid pumped from the right ventricle, the afterload line and the return line carrying fluid to a pair of inlets formed on the reservoir.

24. The perfusion apparatus of claim 23 further including a first flow probe disposed in the afterload line, and a second flow probe disposed in the return line, said first and second flow probes for measuring flow rates.

25. The perfusion apparatus of claim 18 wherein the venous line includes an afterload line for maintaining an afterload pressure against which the heart beats, the afterload line being adjustable for controlling the afterload pressure.

26. The perfusion apparatus of claim 18 further including a pressure sensing device inserted into the right ventricle for measuring an intracavity pressure within the right ventricle.

27. A portable perfusion apparatus for preserving a harvested donor heart in a beating state comprising:
a preservation chamber for storing the heart during a preservation period;
a perfusion circuit associated with the preservation chamber for circulating blood to and from the heart, said perfusion circuit including an arterial line for providing oxygenated blood to the heart, and a pair of venous lines for carrying depleted blood away from the heart, one of said venous lines forming an afterload column for maintaining an afterload pressure against which the heart beats;
a reservoir disposed along the perfusion circuit for storing a predetermined quantity of blood, said reservoir having at least one inlet for receiving blood from the perfusion circuit, and one outlet for supplying blood to the perfusion circuit;
a pump for circulating blood through the arterial line of the perfusion circuit;
an oxygenating device disposed along the perfusion circuit for oxygenating said blood with a mixture of oxygen and carbon dioxide;
a temperature control device operably associated with the perfusion circuit for maintaining the heart at a normothermic temperature; and
a blood filtering device disposed along the perfusion circuit for removing unwanted material from the blood;
wherein said perfusion circuit, said pump, said oxygenating device, and said temperature control device simulate the donor cardiovascular system by maintaining physiologic levels for temperature, oxygenation and flow rate; and wherein said organ is an integrated element of said perfusion circuit.

28. The perfusion apparatus of claim 27 wherein the perfusion circuit is coated with a heparin surface for contacting the blood circulating therethrough.

29. The perfusion apparatus of claim 27 wherein the preservation chamber includes:
a side wall portion having an open top portion, the side wall portion having a flange extending from its top surface;
a bottom portion connected to a lower end of the side wall portion; and
a cover assembly for engaging the flange and sealing the preservation chamber, the cover assembly having a cover plate bounded by a clamp member.

30. The perfusion apparatus of claim 27 including a drip manifold connected to the oxygenating device for delivering a plurality of chemical solutions into the perfusion circuit.

31. The perfusion apparatus of claim 27 further including a mobile cart for supporting the preservation chamber and perfusion circuit, and for transporting the heart being preserved by the perfusion apparatus.

32. A preservation chamber for containing an organ comprising:
  a side wall portion having an open top portion, the side wall portion having a flange extending from its top surface;
  a bottom portion connected to a lower end of the side wall portion; and
  a cover assembly for engaging the flange and sealing the preservation chamber, the cover assembly having a cover, plate bounded by a clamp member.

33. The preservation chamber of claim 32 including a cannula plate for supporting a plurality of cannulas.

34. The preservation chamber of claim 32 wherein the cannula plate and the cover plate include a tongue and groove mechanism for engaging one another.

35. The preservation chamber of claim 32 wherein the clamp member includes a hinge mechanism on one side thereof, and a locking mechanism opposite the hinge mechanism.

36. The preservation chamber of claim 32 wherein the bottom member is sloped for promoting flow of a fluid therein to a drain portion.

* * * * *

UNITED STATES PATENT AND TRADEMARK OFFICE
CERTIFICATE OF CORRECTION

PATENT NO. : 6,100,082
DATED : August 8, 2000
INVENTOR(S) : Waleed H. Hassanein

Page 1 of 1

It is certified that error appears in the above-identified patent and that said Letters Patent is hereby corrected as shown below:

Column 12, claim 2,
Line 33, delete "normothermic" and instead insert -- physiologic --;
Line 33, between "temperature" and "simulate" insert --, oxygenation and flow rate --;
Lines 34-35 delete "is maintained in the normal beating state by the perfusion apparatus" and instead insert -- continues to beat at a physiologic heart rate --;

Claim 10,
Line 60, change the dependency from "claim 4" to -- claim 9 --;

Column 15, claim 32,
Line 10, delete the "," and before the "." insert -- ; and a cannula plate for supporting a plurality of cannulas --;
Delete claim 33 in its entirety;

Column 16,
Renumber claims 34-36 as 33-35, respectively.

Signed and Sealed this

Ninth Day of October, 2001

Attest:

*Nicholas P. Godici*

NICHOLAS P. GODICI
Attesting Officer
*Acting Director of the United States Patent and Trademark Office*

UNITED STATES PATENT AND TRADEMARK OFFICE
Certificate

Patent No. 6,100,082                                                                                    Patented: August 8, 2000

On petition requesting issuance of a certificate for correction of inventorship pursuant to 35 U.S.C. 256, it has been found that the above identified patent, through error and without any deceptive intent, improperly sets forth the inventorship.

Accordingly, it is hereby certified that the correct inventorship of this patent is: Waleed H. Hassanein, North Andover, MA (US); Shukri F. Khuri, Westwood, MA (US); Michael D. Crittenden, Hyde Park, MA (US); and Vladimir Birjiniuk, Weston, MA (US).

Signed and Sealed this Seventeenth Day of July 2007.

GLADYS J.P. CORCORAN
*Supervisory Patent Examiner*
Art Unit 1744